(12) United States Patent
Kolter et al.

(10) Patent No.: US 8,865,250 B2
(45) Date of Patent: Oct. 21, 2014

(54) PRODUCTION OF PULVERULENT COATING COMPOSITIONS FOR STABLE PROTECTIVE COATINGS FOR PHARMACEUTICAL DOSAGE FORMS

(75) Inventors: Karl Kolter, Limburgerhof (DE); Maximilian Angel, Schifferstadt (DE); Bernhard Linner, Bobenheim-Roxheim (DE)

(73) Assignee: BASF SE, Ludwigshafen (DE)

( * ) Notice: Subject to any disclaimer, the term of this patent is extended or adjusted under 35 U.S.C. 154(b) by 100 days.

(21) Appl. No.: 13/406,626

(22) Filed: Feb. 28, 2012

(65) Prior Publication Data

US 2012/0219694 A1 Aug. 30, 2012

Related U.S. Application Data

(60) Provisional application No. 61/447,122, filed on Feb. 28, 2011.

(51) Int. Cl.
*A61K 9/28* (2006.01)
*A61K 47/32* (2006.01)
*C09D 5/03* (2006.01)

(52) U.S. Cl.
CPC .............. *A61K 47/32* (2013.01); *A61K 9/2846* (2013.01); *C09D 5/03* (2013.01)
USPC .......................................... 427/2.14; 427/2.1

(58) Field of Classification Search
USPC ................................... 260/885; 427/2.1, 2.14
See application file for complete search history.

(56) References Cited

U.S. PATENT DOCUMENTS

| | | | |
|---|---|---|---|
| 4,433,076 A | 2/1984 | Bauer et al. | |
| 4,816,558 A | 3/1989 | Rauch et al. | |
| 6,281,282 B1 | 8/2001 | Breitenbach et al. | |
| 6,624,210 B1 | 9/2003 | Petereit et al. | |
| 6,696,085 B2 | 2/2004 | Rault et al. | |
| 2003/0064036 A1 | 4/2003 | Petereit et al. | |
| 2004/0152867 A1 | 8/2004 | Omote et al. | |
| 2004/0249035 A1 | 12/2004 | Petereit et al. | |
| 2011/0033532 A1 | 2/2011 | Angel et al. | |
| 2012/0076858 A1 | 3/2012 | Kolter et al. | |

FOREIGN PATENT DOCUMENTS

| | | |
|---|---|---|
| CA | 1009144 | 4/1977 |
| DE | 1090381 | 10/1960 |
| DE | 1219175 | 6/1966 |
| DE | 2135073 | 2/1973 |
| DE | 2512238 | 5/1976 |
| DE | 3049179 | 7/1982 |
| EP | 0088951 | 9/1983 |
| EP | 0262326 | 4/1988 |
| GB | 1097054 | 12/1967 |
| WO | WO-97/42255 | 11/1997 |
| WO | WO-00/05307 | 2/2000 |
| WO | WO0188021 | * 11/2001 ............... A61K 9/28 |
| WO | WO-02/067906 | 9/2002 |
| WO | WO-2004/019918 | 3/2004 |
| WO | WO-2009/016258 | 2/2009 |
| WO | WO-2010/139654 | 12/2010 |
| WO | WO-2011/051155 | 5/2011 |
| WO | WO-2012/031934 | 3/2012 |
| WO | WO-2012/041788 | 4/2012 |
| WO | WO-2012/116940 | 9/2012 |

OTHER PUBLICATIONS

"Machine Translation of DE1090381", 2 pages.
*Thompson Scientific*, London BG XP-002673622 Nov. 22, 2001, 2 pgs.
PCT International Search Report in PCT/EP2012/053232, dated Apr. 26, 2012, , 4 pgs.
Huanan Ligong, Daxue X., "Influences of inlet and outlet drying temperatures on re-dispersible EVA polymer powders", *Journal of South China University of Technology (Natural Science)* XP-002673623 Jul. 2007, 1 pg.

\* cited by examiner

*Primary Examiner* — Dah-Wei D. Yuan
*Assistant Examiner* — Andrew Bowman
(74) *Attorney, Agent, or Firm* — Servilla Whitney LLC

(57) ABSTRACT

Described are processes for producing pulverulent coating compositions comprising providing an aqueous polymer dispersion comprising
  i) as component A a polymer obtained by radical polymerization of
    a) N,N-diethylaminoethyl methacrylate, and
    b) at least one radically polymerizable compound selected from esters of $\alpha,\beta$-ethylenically unsaturated mono- and dicarboxylic acids with $C_1$-$C_8$-alkanols; and
spray processing the aqueous polymer dispersion in the presence of a drying gas to provide a powder, wherein the entry temperature of the drying gas into the spraying apparatus is at least 20° C. above the glass transition temperature and is at least 20° C. above the minimum film-forming temperature of the polymer and the exit temperature of the drying gas from the spraying apparatus is kept at 40 to 85° C.

20 Claims, No Drawings

PRODUCTION OF PULVERULENT COATING COMPOSITIONS FOR STABLE PROTECTIVE COATINGS FOR PHARMACEUTICAL DOSAGE FORMS

CROSS-REFERENCE TO RELATED APPLICATIONS

This application claims priority under 35 U.S.C. §119(e) to U.S. Provisional Application No. 61/447,122, filed Feb. 28, 2011, the disclosure of which is incorporated herein by reference in its entirety.

FIELD OF THE INVENTION

Embodiments of the present invention relate to the production of pulverulent coating compositions for stable protective coatings for pharmaceutical dosage forms, as well as processes for redispersing the powders.

BACKGROUND

For the provision of binders for drug coatings with a low residual monomer content, DE-B 2512238 teaches the use of a powder obtained by spray drying a polymer dispersion for producing coating solutions for these drug forms. With regards to the dispersions used for the spray drying, reference is made to DE 1090381, DE 1219175 and DE 2135073.

DE 3049179 A1 is an application of addition to DE 2512238 and relates to the use of a powder obtained by spray drying according to the teaching of the last-mentioned document in the form of an aqueous suspension, which additionally comprises a plasticizing agent, for producing coatings by thermogelation.

WO 00/05307 deals with the provision of coating and binding compositions for drug forms which comprise (meth) acrylate copolymers which have monomer radicals with tertiary amino groups, the intention being for simple dry or aqueous further processing to be possible. In addition, this document teaches a process in which (a) a copolymer of $C_1$-$C_4$-esters of (meth)acrylic acid and (meth)acrylate monomers which have tertiary ammonium groups, (b) a plasticizer and (c) an emulsifier with an HLB value of at least 14 are combined with one another and the coating or binding composition is produced therefrom by melting, pouring, spreading or spraying, where the copolymer (a) is incorporated in powder form with an average particle size from 1 to 40 μm. The processability achieved here is attributed to the provision of the copolymer (a) in powder form with an extremely small particle size.

WO 02/067906 relates to coating and binding compositions having improved water-vapor permeability compared with those described in WO 00/05307. Here, the coating and binding compositions are produced using a mixture which comprises (a) a copolymer of $C_1$-$C_4$-esters of (meth)acrylic acid and further (meth)acrylate monomers with functional tertiary ammonium groups in powder form having an average particle size from 1 to 40 μm, (b) an emulsifier with an HLB value of at least 14 and (c) a $C_{12}$-$C_{18}$-monocarboxylic acid or a $C_{12}$-$C_{18}$-hydroxyl compound.

WO 2004/019918 describes coating and binding compositions which correspond to those described in WO 00/05307 and WO 02/067906 as regards their composition.

According to U.S. Pat. No. 6,696,085 B2, a methacrylic acid copolymer type C is reportedly used as disintegrant. The methacrylic acid copolymer type C is an enteric polymer which is not soluble in the acidic pH range, but is water-soluble in the pH range of 7, as is present in the oral cavity. Besides a low fracture strength (<20N), the tablets have a high friability (>7%) and include a high proportion, in the region of 15% by weight, of coarsely particulate disintegrant. Consequently, they have low mechanical strength and, on account of the high proportion of coarsely particulate disintegrant, have an unpleasant sandy feel in the mouth.

EP88951 A2 describes a process for coating drugs using a water-dispersed coating composition based on emulsion polymers, where the coating compositions may be partially present in salt form. The coating compositions can also be obtained from redispersed powders, with the processes of spray drying and of freeze drying being specified as methods that are suitable in principle. However, in this connection, it is also stated that the freeze drying may also be able to be used at the lower limit of the range of suitable glass transition temperatures. Either powders obtained by freeze drying or a spray-dried product of 30% methacrylic acid and 70% methyl methacrylate, which has a high glass transition temperature on account of its composition, are specifically described.

WO 97/42255 describes the spray drying of polymer powders that can be redispersed in aqueous solution and comprise free acid- or base-carrying copolymers by spray drying, where, before the spray drying, the pH values of the dispersions have to be adjusted with the help of a buffer system.

EP 262326 A2 describes a process for producing a redispersible plastics polymer in which an aqueous dispersion of a copolymer of (meth)acrylic acid and (meth)acrylic acid esters with a minimum film-forming temperature below 60° C. and a dynamic glass transition temperature below 150° C. is spray dried such that the entry temperature of the drying gas is above the minimum film-forming temperature and below the glass transition temperature.

WO 2009/016258 discloses the production of the aqueous polymer dispersions of cationic polymers based on N,N-diethylaminoethyl methacrylate as are used according to the invention and the use thereof for the coating of drugs. Use in powder form is only mentioned in quite general terms. In addition, on account of their low glass transition temperature, the polymers may exhibit an undesired tendency towards agglomeration and therefore make high demands from a processing point of view.

There is a need for free-flowing pulverulent film coating compositions with good redispersibility in water which are suitable for pharmaceutical dosage forms which, even upon prolonged or thermally demanding storage, have no change in the release behavior. One requirement for such redispersed coating compositions is the generation of small-particle dispersions with narrow particle size distributions and the avoidance of coagulation.

SUMMARY

According to one aspect of the present invention, provided is a process for producing pulverulent coating compositions comprising providing an aqueous polymer dispersion comprising:
  i) as component A, a polymer obtained by radical polymerization of
    a) N,N-diethylaminoethyl methacrylate, and
    b) at least one radically polymerizable compound selected from esters of α,β-ethylenically unsaturated mono- and dicarboxylic acids with $C_1$-$C_8$-alkanols, and spray processing the aqueous polymer dispersion in the presence of a drying gas to provide a powder. In one or more embodiments of this aspect, the entry temperature of the drying gas into the spraying apparatus is at least 20° C. above the glass transition temperature and is at least 20° C. above the minimum film-forming temperature of the polymer, and the exit temperature of the drying gas from the spraying apparatus is maintained at 40 to 85° C. In some embodiments, the entry temperature of the drying gas into the spraying apparatus is at least 40° C. above the glass transition temperature and is at least 40° C. above the minimum film-forming temperature of the polymer. According to one or more embodiments, the entry temperature of the drying gas into the spraying apparatus is at least 20° C. above the dynamic glass transition temperature. In further embodiments, the entry temperature of the drying gas into the spraying apparatus is at least 40° C. above the dynamic glass transition temperature. In a particular embodiment, the entry temperature of the drying gas into the spraying apparatus is 100 to 140° C. and the exit temperature of the drying gas from the spraying apparatus is maintained at 45 to 70° C. Some embodiments provide that the exit temperature of the drying gas from the spraying apparatus is maintained within 5° C. of the minimum film-forming temperature.

According to one or more embodiments, the spray processing includes spray drying or agglomerating spray drying.

The polymer powder or a dispersion comprising the powder may further comprise an acid or acidic salt. In one or more embodiments, an acid or an acidic salt is added to the aqueous polymer dispersion before the spray processing and/or is added to the powder after the spray processing. One or more embodiments provide that, after the spray processing, the resulting polymer powder is redispersed in water and admixed with an acid or an acidic salt. In some embodiments, the acid added is an acid or an acidic salt thereof which is decomposed or evaporated under the conditions of the spray processing. According to one or more embodiments, as a result of adding the acid or the acidic salt, the pH of the aqueous dispersion, of the powder, or of the redispersion is in the range from 5 to 9. In some embodiments, adding the acid or the acidic salt results in the pH of the aqueous dispersion, of the powder, or of the redispersion being in the range from 6 to 8.

In some embodiments, a further auxiliary is added to the aqueous polymer dispersion before the spray processing.

In one or more embodiments, silicon dioxide is added to the resulting polymer powder during or after the spraying process.

Another aspect of the present invention provides a method of coating a pharmaceutical dosage form comprising applying a polymer powder obtained according to the first aspect as a coating composition to the pharmaceutical dosage form.

According to one or more embodiments of this aspect, the coating composition is applied to the dosage form in the form of an aqueous dispersion obtained by redispersing the polymer powder. In one or more embodiments, redispersing the polymer powder comprises stirring the powder in water with a dispersing apparatus at revolutions of greater than 5000 rpm. In other embodiments, redispersing the polymer powder comprises stifling the powder in water with a dispersing apparatus at revolutions of less than 1000 rpm. According to one or more embodiments, the polymer powder is ground on its own or together with additional auxiliaries before redispersing.

In some embodiments, the coating composition further comprises one or more auxiliaries selected from the group consisting of aroma substances, taste-improving substances, sweetening agents, glidants, wetting agents, release agents, antisticking agents, stabilizers, antioxidants, pore formers, neutralizing agents, luster agents, dyes, pigments, disinfectants or preservatives, thickeners and plasticizers.

DETAILED DESCRIPTION

Accordingly, a process for producing pulverulent coating compositions from aqueous polymer dispersions comprising,
i) as component A, a polymer obtained by radical polymerization of
   a) N,N-diethylaminoethyl methacrylate, and
   b) at least one radically polymerizable compound selected from esters of $\alpha,\beta$-ethylenically unsaturated mono- and dicarboxylic acids with $C_1$-$C_8$-alkanols, has been found, wherein the aqueous polymer dispersion is converted to free-flowing powders by spraying processes in the presence of a drying gas, where the entry temperature of the drying gas into the spraying apparatus is at least 20° C. above the glass transition temperature and at least 20° C. above the minimum film-forming temperature of the polymer and the exit temperature of the drying gas from the spraying apparatus is kept at 40 to 85° C.

According to a further embodiment, the entry temperature of the drying gas is at least 20° C. above the glass transition temperature and at least 20° C. above the dynamic glass transition temperature and at least 20° C. above the minimum film-forming temperature of the polymer and where the exit temperature of the drying gas from the spraying apparatus is 40 to 85° C.

Preferably, the entry temperature of the drying gas into the spraying apparatus is at least 40° C. above the glass transition temperature and at least 40° C. above the minimum film-forming temperature of the polymer.

According to one embodiment of the invention, the entry temperature of the drying gas is at least 20° C. above the glass transition temperature. In some embodiments, the entry temperature of the drying gas is at least 40° C. above the dynamic glass transition temperature and at least 40° C. above the minimum film-forming temperature of the polymer.

For any of the aforementioned embodiments, the exit temperature of the drying gas may be in the range from 45 to 70° C.

According to a further preferred embodiment, the conversion to free-flowing powders takes place by agglomerating spray drying.

According to a further preferred embodiment, the polymers are partially neutralized with acids before or after the spraying process.

A further embodiment relates to carrying out a spraying process in the presence of further polymers and/or further auxiliaries.

Furthermore, the use of the powders obtained in this way as pharmaceutical coating compositions has been found. Preferably, the coating compositions are obtained by redispersion in water, the powder obtained by a spraying process being redispersed using low-shear stirring apparatuses at revolutions up to 1000 rpm. Surprisingly, it is also possible to use high-shear dispersing apparatuses at revolutions of >5000 rpm. This can take place according to the invention without the fine particles formed during the redispersion agglomerating and the preparation coagulating. Free-flowing powders within the context of the one or more embodiments of the present invention means that the powders, upon determining the flowability in accordance with DIN ISO 4324 using Pfrengle equipment without stirring aid, flow out of the funnel freely and completely.

The coating compositions used for the spraying processes are based on aqueous polymer dispersions which are obtained by radical emulsion polymerization of a monomer mixture M) comprising
  a) N,N-diethylaminoethyl methacrylate, and
  b) at least one radically polymerizable compound selected from esters of α,β-ethylenically unsaturated mono- and dicarboxylic acids with $C_1$-$C_8$-alkanols,
in an aqueous medium at a pH of at least 8.

The coating compositions in the form of aqueous polymer dispersions preferably comprise no additional organic solvents.

According to one or more embodiments of the invention, the coating compositions serve for producing pharmaceutical dosage forms which are intended to be released rapidly in the acidic environment of the stomach, i.e. the coatings are soluble in gastric juice. In some embodiments, released rapidly means that after 60 min at least 80% of the active ingredient has been released. According to some embodiments, the coatings are not intended to dissolve in the oral cavity and throat in the neutral or virtually neutral environment of the saliva.

The coating compositions can be used for taste masking or for protection against moisture. The water-vapor permeability of the coatings is very low, as a result of which moisture-sensitive active ingredients are protected.

For producing the polymers by radical emulsion polymerization, reference is expressly made here to the disclosure of WO 2009/016258, in which the production and preferred embodiments with regard to production and also composition are described in detail.

In one or more embodiments, a polymer dispersion is used which is obtained from a monomer mixture M) which consists of
  43 to 47% by weight, based on the total weight of the monomers used for the polymerization, of N,N-diethylaminoethyl methacrylate a), and
  53 to 57% by weight, based on the total weight of the monomer used for the polymerization, of at least one compound b), in particular methyl methacrylate.

The polymers present in the dispersions preferably have an average molecular weight $M_w$, determined by means of gel permeation chromatography, in the range from 30 000 to 500 000, particularly preferably 60 000 to 140 000, in particular 80 000 to 120 000 g/mol.

The polymers present in the dispersions Pd) preferably have a K value (determined in accordance with Fikentscher on a 1% strength solution in N-methylpyrrolidone (NMP)) in the range from 40 to 60.

The glass transition temperature $T_G$ determined by means of DSC "Differential Scanning Calorimetry" is preferably in a range from 40 to 70° C., particularly preferably 52 to 62° C. Here, the samples are firstly heated to 150° C. and then rapidly cooled from 150° C. The measurement of the glass transition temperature takes place at a heating rate of 20° K/min.

The minimum film-forming temperature is determined according to the method described in DIN ISO 2115 and is in the range from 40 to 70° C., preferably 50 to 65° C. The measurement accuracy of the method is in the region of +/−5° C.

In one or more embodiments, the polymers present in the dispersions are essentially random copolymers.

The average particle diameter of the polymer particles present in the polymer dispersion (determined by means of analytical ultracentrifuge) is preferably in a range from 70 to 200 nm, particularly preferably from 80 to 150 nm, in particular from 90 to 120 nm. The particle size distribution is preferably essentially unimodal.

The LT value of the dispersions, determined on a 0.01% strength dispersion in water (2.5 cm cuvette, white light), is preferably at least 70%, particularly preferably at least 80%. The determination of the light transmission is described e.g. in Dieter Distler, Wassrige Polymerdispersionen [Aqueous polymer dispersions], Wiley-VCH (1999), p. 40.

The solids content of the dispersions used for the spraying processes is preferably 10 to 50% by weight, particularly preferably 20 to 40% by weight. In the case of a prior purification of the dispersion by means of ultrafiltration, the dispersions used may have solids contents which are within these ranges before and after the ultrafiltration. It is of course likewise possible to subject a dilute polymer dispersion to concentration by ultrafiltration before the spraying process.

The redispersible polymer powders used for taste masking have, in water at a solids content of 20% by weight, low viscosities of preferably less than 300 mPas, particularly preferably less than 200 mPas and in particular less than 100 mPas (values determined by means of Brookfield viscometer at 20° C. and 100 $s^{-1}$). Such viscosities are of particular importance for many applications.

According to one or more embodiments of the invention, the conversion of the aqueous polymer dispersions to the powder form takes place by means of spray processes. Suitable spray processes include, but are not limited to, spray drying, agglomerating spray drying, spray granulation (spray fluidized-bed drying) or spray agglomeration.

The conditions specified below for carrying out the atomization and drying refer to all embodiments of the spraying process which can be carried out in principle, whether normal spray drying, spray granulation or agglomerating spray drying.

The atomization preferably takes place as hydrodynamic atomization as a result of liquid pressure or air pressure via nozzles such as, for example, single-material or multiple-material nozzles or via atomizing disks.

Suitable spraying apparatus are conventional spray towers into which the polymer dispersion to be atomized is introduced from above. The polymer powders obtained can be discharged at the lower end and be separated off from the drying-gas steam in a downstream cyclone.

Drying gases which can be used are air or inert gases such as nitrogen, argon or helium. The drying gases can be introduced countercurrently or cocurrently to the liquid droplets produced by the atomization through the spraying apparatus. The drying gas is preferably used cocurrently. The entry temperature of the drying gas is kept at least 20° C., preferably at least 40° C., above the glass transition temperature and, according to one embodiment, also at least 20° C., preferably at least 40° C., above the dynamic glass transition temperature and at least 20° C., preferably at least 40° C., above the minimum film-forming temperature of the polymer. In some embodiments, the entry temperature of the drying gas into the spraying apparatus is particularly preferably kept at 100 to 140° C. and the exit temperature of the drying gas from the spraying apparatus is kept at 45 to 70° C. In some embodiments, the entry temperature of the drying gas into the spraying apparatus is kept at 110 to 130° C. and the exit temperature of the drying gas from the spraying apparatus is kept at 50 to 60° C. The exit temperature of the drying gas may be in the same temperature range plus/minus 5° C. as the minimum film-forming temperature.

The evaporation of the water in the spraying apparatus can take place either at atmospheric pressure or at 0.06 to 0.12 MPa.

While carrying out the spraying processes, polymeric spraying auxiliaries such as polyvinyl alcohols, mixtures of polyvinyl alcohol and a graft copolymer consisting of polyethylene glycol as graft base and polyvinyl alcohol side chains (commercially available as Kollicoat® Protect), polyvinylpyrrolidones, alkylated and/or hydroxyalkylated celluloses, starch derivatives, ligninsulfonates, polyacrylic acids or polyacrylamides can also be added to the aqueous polymer dispersions. Suitable amounts of such spraying auxiliaries are in the range from 0.1 to 30, preferably 1 to 10% by weight, based on the solids content.

Furthermore, antiblocking agents can also be added to the aqueous polymer dispersions. Suitable antiblocking agents are e.g. aluminum silicates such as bentonite, also kieselguhr, colloidal silica, precipitated silica, diatomaceous earth, calcium carbonate, titanium dioxide, zinc oxide, magnesium silicates such as talc or tricalcium phosphate. Suitable amounts of such antiblocking agents are in the range from 0.1 to 15, preferably 0.5 to 5% by weight, based on the solids content.

In principle, customary coating auxiliaries can also be added to the aqueous polymer dispersions. Suitable auxiliaries may be: aroma substances, taste-improving substances, sweetening agents (sugars, sugar alcohols, sweeteners such as aspartame, saccharine-Na, sodium cyclamate), glidants, wetting agents, release agents, antisticking agents, stabilizers, antioxidants, pore formers, neutralizers, luster agents, dyes, pigments, disinfectants or preservatives, thickeners or plasticizers. Suitable auxiliaries are described e.g. in Fiedler, H. P. Lexikon der Hilfsstoffe für Pharmazie, Kosmetik and angrenzende Gebiete [Lexicon of auxiliaries for pharmacy, cosmetics and related fields], 4th edition, Aulendorf: ECV-Editio-Cantor-Verlag, 1996.

As already mentioned, one embodiment of the invention relates to conventional spray drying, during which the aqueous polymer dispersion to be dried is atomized and dried in the gas stream of the drying gas and in this way converted to powder form.

According to a further embodiment, the conversion to powder can take place by a spray granulation. For this purpose, the aqueous polymer dispersion to be dried is likewise atomized and the particles generated then come into contact in a fluidized bed with seed particles that have been introduced as initial charge. As a result of this bringing of the seed particles into contact with the droplets of the aqueous polymer dispersion, the seed particles grow to give larger granule particles, with the formation of an onion-peel-like structure around the particle used as seed material.

According to one or more embodiments of the invention, conversion to the powder form takes place with the help of agglomerating spray drying. Here, the polymer dispersion is atomized in a spray tower as described above, while fine dust which is removed from the drying zone, is at the same time blown into the atomizing zone, in which the aqueous polymer dispersion is present in the form of fine droplets. The fine dust particles stick together here to give relatively large aggregates with a blackberry-shaped structure. Additionally, a fluidized bed can also be connected, in which the water content of the particles formed can be further reduced. The resulting aggregates can have particle sizes from 150 to 1000 µm, preferably from 200 to 500 µm. In this embodiment too, the entry temperature is selected at least 20° C. and preferably at least 40° C., above the glass transition temperature, and, according to one embodiment, also at least 20° C., preferably at least 40° C., above the dynamic glass transition temperature and at least 20° C., preferably at least 40° C., above the minimum film-forming temperature of the polymer, and the exit temperature of the drying gas from the spray apparatus is selected at 40 to 85° C., preferably at 45 to 70° C. Preferably, the entry temperature of the drying gas into the spraying apparatus is kept at 100 to 140° C. and the exit temperature of the drying gas from the spraying apparatus is kept at 45 to 70° C. In some embodiments, the entry temperature of the drying gas into the spraying apparatus is kept at 110 to 130° C. and the exit temperature of the drying gas from the spray apparatus is kept at 50 to 60° C. The blackberry-shaped structures obtained by spray agglomeration are virtually dust-free and exhibit particularly advantageous behavior upon redispersion.

In all of the embodiments specified above, spraying auxiliaries such as e.g. aluminum silicates such as bentonite, kieselguhr, colloidal silica, precipitated silica, diatomaceous earth, calcium carbonate, titanium dioxide, zinc oxide, magnesium silicates such as talc or tricalcium phosphate can be blown in to the spray tower during the spraying process in amounts of from 0.1 to 15, preferably 0.5 to 5% by weight, based on the polymer powder.

The residual solvent content is usually not more than 5% by weight, based on the solids content of the powder.

In total, the particle sizes of the powder formed by spray processes are governed by the particular variant. In the case of a normal spray drying, average particle sizes from 10 to 150 µm can be achieved. In the case of a spray granulation, such as, for example, a spray fluidized-bed drying, larger particle sizes from 150 up to 1000 µm can be achieved. In the case of agglomerating spray drying, particle sizes from 150 to 1000 µm can be achieved.

According to a further embodiment, acids are added to the polymer. Preferably, amounts of acid are added such that the basic groups are present partially in the form of the acid salts. Preferably, 1 to 20 mol %, particularly preferably 2 to 15 mol %, of the basic groups are neutralized. This can take place before or after the spray drying. Thus, for example, the acid can be added to the aqueous polymer dispersion before the spray drying. According to another embodiment, the acid can also be added before or during the redispersion. If the incorporation of the acid takes place before the spray drying, then it can be stirred into the aqueous dispersion by means of customary processes. In the case of addition after the spray drying, the incorporation of the acid into the polymer powder takes place such that firstly the polymer powder is coarsely predispersed in water by means of a simple stirrer, then the acid is added and complete redispersion is achieved by further stifling. The redispersion is very rapid and therefore even after 10 min, finely divided dispersates are present. In a modified procedure, it is also possible to firstly introduce the acid as initial charge in water and to add the polymer powder to this with stirring. It is also possible to firstly mix polymer powder and acid and to introduce this powder mixture into water.

Suitable acids are inorganic acids or acid salts such as carbonic acid (injection of carbon dioxide), ammonium hydrogencarbonate, sodium hydrogencarbonate, hydrochloric acid, sulfuric acid or phosphoric acid or phosphoric acid salts such as sodium dihydrogenphosphate. Also of suitability are organic acids such as tartaric acid, citric acid, lactic acid, glycolic acid, malic acid, malonic acid, maleic acid, succinic acid, fumaric acid, aspartic acid, glutamic acid, gluconic acid or further physiologically compatible acids. Polymeric acids on a natural and/or synthetic base are of course also possible. The specified acids are suitable for all of the described embodiments.

According to a further embodiment of the invention, acids which are decomposed or which evaporate under the conditions of the spraying process are used. According to this embodiment, the polymers are present before and during the spraying process in neutralized or partially neutralized form, whereas in the resulting powder the free basic form is present again.

The amounts by weight of acids to be used in individual cases is governed by the particular molecular weight and the above-described desired degree of neutralization.

Preferably, the treatment with acids is carried out such that the pH of the aqueous dispersion, of the powder or of the water-redispersed powder is in the range from 5 to 9.

In some embodiments, the addition of the acid or of the acidic salt is added such that the pH of the aqueous dispersion, of the powder or of the water-redispersed powder is in the range from 6 to 8.

Coating compositions can be produced e.g. by intimately mixing a by redispersing the polymer powder obtained according to the invention to give an aqueous polymer dispersion, to which preferably at least one further auxiliary is added.

According to one preferred embodiment, silicon dioxide is added to the resulting polymer powder during or after the spraying process.

Suitable additional auxiliaries may be: aroma substances, taste-improving substances, sweetening agents (sugars, sugar alcohols, sweeteners such as e.g. aspartame, saccharine-Na, sodium cyclamate), glidants, wetting agents, release agents, antisticking agents, stabilizers, antioxidants, pore formers, neutralizing agents, luster agents, dyes, pigments, disinfectants or preservatives, thickeners, plasticizers etc. Such substances are described e.g. in Fiedler, H. P. Lexikon der Hilfsstoffe für Pharmazie, Kosmetik and angrenzende Gebiete [Lexicon of auxiliaries for pharmacy, cosmetics and related fields], 4th edition, Aulendorf: ECV-Editio-Cantor-Verlag, 1996.

According to one embodiment of the invention, the N,N-diethylaminoethyl methacrylate-based polymer powder is ground before the redispersion in water for producing the coating composition. The grinding can also take place in the presence of the stated additional auxiliaries.

Customary amounts of the auxiliaries are in a range from in each case 0 to 70% by weight, preferably 0 to 60% by weight, in particular 1 to 50% by weight, based on the total weight of the solid of the coating composition.

The coating composition obtained from the powders according to the invention can, however, also be applied to the pharmaceutical dosage forms in powder form. The application can also take place in aqueous form by granulation, pouring, spreading or by means of spray application.

In some embodiments, the application uses aqueous polymer dispersion obtained by redispersing. In principle, any dispersing apparatus is suitable for the redispersion. In this connection, the redispersion preferably takes place with the application of low shear forces, preferably by means of a blade, propeller, anchor stirrer or a comparable stifling tool. The polymer powders according to the invention are hereby redispersed spontaneously and rapidly. The redispersion of the polymer powders in water is usually completed in 10 min.

Further components required for the coating application can be added to these redispersed preparations. Such components are in particular plasticizers such as e.g. triethyl citrate, tributyl citrate, diethyl sebacate, dibutyl sebacate, acetyl triethyl citrate.

Surprisingly, the finely divided dispersions also withstand very high shear forces such as for example in a rotor-stator apparatus, which is also called Ultra-turrax or a colloid mill. The introduction of high shear forces is regulated in a rotor-stator apparatus via the number of revolutions of the apparatus. Preferably, the redispersion takes place with the help of a dispersing apparatus at <5000 rpm. This process is particularly advantageous if further coarsely particulate additives or agglomerated additives additionally have to be incorporated into the dispersion which necessitate a special comminution. The separate comminution of these additives in water and subsequent addition to the redispersed polymer powder is thus dispensed with.

In one particular embodiment, the polymer powders redispersable according to the invention are mixed with further customary coating constituents and/or additives described above to produce so-called ready-to use preparations which comprise all of the required constituents of a coating. These are present in powder or granule form. The user only needs to stir them into water to produce a ready-to-spray suspension. These ready-to-use preparations are produced by dry mixing, grinding, compaction or granulation of the constituents using a granulating liquid, followed by a drying step. In particular, acids or acidic salts which assist the redispersion can be incorporated in this way.

Unless stated otherwise, all of the data within the context of the present invention relating to the average particle size of powders in the micrometer range is the volume average of the particle diameters (d4,3 value) determined by means of light diffraction.

The coating compositions according to the invention can additionally comprise at least one further polymer component. In this connection, mixtures of at least two dispersions, at least one dispersion and at least one solution, at least one dispersion and at least one powder, at least two powders, etc. can be used.

The coating compositions according to the invention are suitable for dosage forms of in principle any desired pharmaceutical active ingredients, which can preferably be administered in isolated or protected form, such as antidepressants, beta receptor blockers, antidiabetic agents, analgesics, antiphlogistics, antirheumatics, antihypotensives, antihypertensives, psychoactive drugs, tranquilizers, antiemetics, muscle relaxants, glucocorticoids, agents for treating ulcerative colitis or Crohn's disease, antiallergic agents, antibiotics, antiepileptics, anticoagulants, antimycotics, antitussives, arteriosclerotic agents, diuretics, enzymes, enzyme inhibitors, gout remedies, hormones and inhibitors thereof, cardiac glycosides, immunotherapeutic agents and cytokines, laxatives, antilipanic agents, gastrointestinal therapeutic agents, antimigrane agents, preparation of mineral substances, otologic agents, agents to treat Parkinson's disease, thyroid therapeutic agents, spasmolytics, platelet aggregation inhibitors, vitamins, cytostatics and metastasis inhibitors, phytopharmaceuticals, chemotherapy agents, nutraceuticals, vitamins, carotenoids and amino acids.

Examples of suitable active ingredients are: acarbose, non-steroidal antirheumatics, cardiac glycosides, acetylsalicylic acid, virustatic agents, aclarubicin, aciclovir, cisplatin, actinomycin, α- and β-sympathomimetics, allopurinol, alosetron, alprostadil, prostaglandins, amantadine, ambroxol, amlodipine, methotrexate, 5-aminosalicylic acid, amitriptyline, amoxicillin, anastrozole, atenolol, atorvastatin, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cephalosporins, celetoxib, cetirizine, chenodeoxycholic acid, ursodeoxycholic acid, theophylline and theophylline derivatives, trypsin, cimetidine, clarithromycin, clavulanic acid, clindamycin, clobutinol, clonidine, cotrimoxazole, codeine, caffeine, vitamin D and derivatives of vitamin D, colestyramine, cromoglycic acid, coumarin and coumarin derivatives, cysteine, cytarabine, cyclophosphamide, cyclosporin, cyproterone, cytarabine, dapiprazole, desogestrel, desonide, dihydralazine, diltiazem, ergot alkaloids, dimenhydrinate, dimethylsulfoxide, dimeticone, dipyridamole, domperidone and domperidone derivatives, donepzil, dopamine, doxazosin, doxorubicin, doxylamine, dapiprazole, benzodiazepine, diclofenac, glycoside antibiotics, desipramine, econazole, ACE inhibitors, enalapril, ephedrine, epinephrin, epoetin and epoetin derivatives, morphinanes, calcium antagonists, irinotecan, modafinil, orlistat, peptide antibiotics, phenytoin, riluzole, risedronate, sildenafil, topiramate, macrolide antibiotics, esomeprazole, estrogen and estrogen derivatives, gestagen and gestagen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, flunarizine, fluorouracil, fluoxetine, flurbiprofen, ibuprofen, flutamide, fluvastatin, follitropin, formoterol, fosfomycin, furosemide, fusidic acid, galantamine, gallopamil, ganciclovir, gemfibrozil, gentamicin, ginkgo, St. John's wort, glibenclamide, urea derivatives as oral antidiabetics, glucagon, glucosamine and glucosamine derivatives, glutathione, glycerol and glycerol derivatives, hypothalamus hormones, goserelin, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramin, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives; evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, orlistat, oseltamivir, oxaceprol, oxacillin, oxiconazole, oxymetazoline, pantoprazole, paracetamol, paroxetine, penciclovir, oral penicillin, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, rosiglitazone, roxatidine, roxithromycin, ruscogenin, rutoside and rutoside derivatives, sabadilla, salbutamol, salmeterol, scopolamine, selegiline, sertaconazole, sertindole, sertraline, silicates, simvastatin, sitosterol, sotalol, spaglumic acid, sparfloxacin, spectinomycin, spiramycin, spirapril, spironolactone, stavudine, streptomycin, sucralfate, sufentanil, sulbactam, sulfonamides, sulfasalazine, sulpiride, sultamicillin, sultiame, sumatriptan, suxamethonium chloride, tacrine, tacrolimus, taliolol, tamoxifen, taurolidine, tazarotene, tegaserod, temazepam, teniposide, tenoxicam, terazosin, terbinafine, terbutaline, terfenadine, terlipressin, tertatolol, tetracyclines, tetryzoline, theobromine, theophylline, butizine, thiamazole, phenothiazines, thiotepa, tiagabine, tiapride, propionic acid derivatives, ticlopidine, timolol, tinidazole, tioconazole, thioguanine, thioxolone, tiropramide, tizanidine, tolazoline, tolbutamide, tolcapone, tolnaftate, tolperisone, topotecan, torasemide, antiestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpine, troxerutin, tulobuterol, tyramine, tyrothricin, urapidil, ursodeoxycholic acid, chenodeoxycholic acid, valaciclovir, valdecoxib, valproic acid, vancomycin, vecuronium chloride, venlafaxine, verapamil, vidarabine, vigabatrin, viloxazine, vinblastine, vincamine, vincristine, vindesine, vinorelbine, vinpocetine, viquidil, warfarin, xantinol nicotinate, xipamide, zafirlukast, zalcitabine, zanamivir, zidovudine, zolmitriptan, zolpidem, zopiclone, zotepine and the like.

If desired, the active ingredients can also be used in the form of their pharmaceutically acceptable salts or derivatives, and in the case of chiral active ingredients, both optically active isomers and also racemates or diastereoisomer mixtures can be used. If desired, the compositions according to the invention can also comprise two or more pharmaceutical active ingredients.

According to the invention, the coating compositions can be used for coating extrudates, minitablets, capsules, soft capsules, granules, pellets, micropellets, microcapsules, nanocapsules or crystals.

For producing dosage forms, the coated granules, pellets, micropellets, microcapsules, crystals can be mixed with suitable auxiliaries and compacted to give tablets, which disintegrate in the aqueous environment of the oral cavity and release the coated fine shaped articles again. Of particular importance in this connection are the so-called oral dispersibles, i.e. tablets which disintegrate in the mouth within a short time and release the taste-masked small shaped articles.

Furthermore, the coating compositions can also be used advantageously for coating tablets.

Active ingredient classes and substances which can often bring about an unpleasant bitter taste and can be formulated advantageously according to the invention are e.g.:

analgesics and antirheumatics, such as paracetamol, diclofenac, aceclofenac, ibuprofen, ketoprofen, flurbiprofen, acetylsalicylic acid, levacetylmethadol and oxycodone;

psychoactive drugs, such as promethazines, donepezil, modafinil, nefazodone, reboxetine, sertindole and sertraline;

antibiotics, such as erythromycin, roxithromycin, clarithromycin, grepafloxacin, ciprofloxacin, levofloxacin, sparfloxacin, trovafloxacin and nevirapine;

beta blockers, such as propranolol, metoprolol, bisoprolol and nebivolol;

antidiabetics, such as metformin, miglitol and repaglinide;

$H_1$ antihistamines, such as diphenhydramine, fexofenadine and mizolastine;

$H_2$ antihistamines, such as cimetidine, famotidine, roxatidine, nizatidine, ticlopidine, cetirizine and ranitidine;

vitamins such as thiamine nitrate and quinidine sulfate, amyloprilose HCl, pseudoephedrine HCl, sildenafil, topiramate, granisetron, rebamipide, quinine HCl, etc.

Also various salts of these active ingredients can be formulated correspondingly.

The exceptional taste masking results from the insolubility of the polymers according to one or more embodiments of the invention at pH values greater than 6 and the rapid solubility at pH values below 6. That is in the saliva (pH: 7.2) correspondingly coated forms are stable for a very long time and there is no contact between the bitter drug and the oral mucosa, but in the stomach at pH values from 1 to 5 there is very rapid release of the active ingredient. The dissolution is so rapid here that there is no difference in the onset of action compared with an uncoated form. As a rule, film coatings of a polymer according to the invention dissolve within 5 min in gastric juice, whereas in phosphate buffer pH 7.2 they are stable for 2 hours. Surprisingly, the film coatings also dissolve relatively quickly in media with pH values of 4.5, meaning that the administration forms produced therefrom develop a rapid effect even in anacidic patients or patients which are treated with antacids. These exceptional application properties of the coating compositions are also retained after the conversion to powders and redispersion of the powders.

Surprisingly, with the help of the process according to the invention, it is possible to convert the aqueous polymer dispersion into free-flowing powders without resulting in relatively large agglomerations and deposits in the spraying apparatus.

It was also surprising for the person skilled in the art that the agglomerating spray drying could be applied so advantageously. The applicability of this technology is all the more surprising as, during it, fine powder particles are blown again in front of the spray nozzle thus to achieve contact with hot entry air, and nevertheless remain dispersible.

In view of the recommendations in the prior art with regard to drying method or temperature control of the drying gases, this had not been expected by the person skilled in the art. It was also surprising that the redispersed finely divided dispersions withstand the use of high shear forces since the person skilled in the art would normally have expected coagulation of the dispersion at shear forces. This is because finely divided dispersions are otherwise sufficiently known for being very sensitive to high shear stresses.

The process according to embodiments of the invention accordingly leads to polymer powders with a good particle size distribution and good application properties such as, for example, flowability. When used for producing coating compositions, the powders can be redispersed very advantageously to give finely divided dispersions. There are often only small differences between the particle sizes of the redispersate and of the original dispersion.

EXAMPLES

Abbreviations Used

Glass transition temperature: Tg
All data in % relate to % by weight.
The preparation of the polymer takes place analogously to example 1 of WO 2009/016258.
Polymer A: Methyl methacrylate/diethylaminoethyl methacrylate, weight ratio 60:40, K value 50, Tg 62° C.
Polymer B: Methyl methacrylate/diethylaminoethyl methacrylate, weight ratio 55:45, K value 49, Tg 57° C.
Polymer C: Methyl methacrylate/diethylaminoethyl methacrylate, weight ratio. 53:47, K value 52, Tg 55° C.
The K values were measured at 0.1% strength by weight in NMP. The polymers were used as 30% strength by weight aqueous dispersions with a pH of 9+/−0.3. The average particle sizes of the primary dispersions were 128, 127 and 131 nm. The glass transition temperatures were determined by means of DSC at a heating rate of 20° K/min. The minimum film-forming temperature corresponded to the Tg within the scope of measurement accuracy of +/−5° C.

When determining the average particle sizes of the powders, the (d4,3) value was determined by light diffraction using a Malvern Mastersizer 2000.

When determining the average particle sizes of the redispersed powders by means of light scattering, the value was determined using a "Malvern Zetasizer nano-s" as intensity average.

Example 1

1000 ml of an aqueous dispersion of polymer B with a solids content of 30% were admixed, with stirring, with 72.9 ml of 1 molar hydrochloric acid. This corresponds to a degree of neutralization of 10 mol %. This partially neutralized dispersion was spray dried in a FSD spray tower, the atomization taking place via a 1.2 mm two-material nozzle at an atomization pressure of 2.5 bar. The entry air temperature was 109° C. and the exit air temperature 54° C. The fines fraction was separated off during the spray drying and blown again in front of the spray nozzle so that spray-dried particles with an average particle size of 180 μm resulted.

The spray-dried product was redispersed in water to give a spray suspension with a solids content of 20% by stirring using a paddle stirrer for 15 min. Measurement of the particle size by means of light scattering gave a value of 128 nm.

Example 2

1000 ml of an aqueous dispersion of polymer A with a solids content of 30% were spray dried in a spray tower. The atomization took place here via a 1.2 mm two-material nozzle at an atomization pressure of 3.0 bar. The drying gas was introduced tangentially in the entry region of the spray dryer and the dried product was separated off in a cyclone. The entry air temperature was 108° C. and the exit air temperature 57° C. The average particle size of the powders was 30 μm.

100 g of spray-dried product were introduced into 900 ml of water, into which 2.55 g of succinic acid had been dissolved beforehand. The preparation was stirred for 20 min using a propeller stirrer. Measurement of the particle size by means of light scattering gave a value of 135 nm.

Example 3

1000 ml of an aqueous dispersion of polymer A with a solids content of 30% were spray dried in a spray tower. The atomization took place here via a 1.2 mm two-material nozzle at an atomization pressure of 3.0 bar. The drying gas was introduced tangentially in the entry region of the spray dryer and the dried product was separated off in a cyclone. The entry air temperature was 110° C. and the exit air temperature 59° C. The average particle size of the powders was 32 μm.

150 g of spray-dried product were introduced into 850 ml of water and the preparation was treated for 20 min using an Ultra-turrax at 12 000 rpm. Measurement of the particle size by means of light scattering gave a value of 270 nm.

Example 4

1000 ml of an aqueous dispersion of polymer B with a solids content of 30% were mixed, with stirring, with 36.5 ml of 1 molar hydrochloric acid. This corresponds to a degree of neutralization of 5 mol %. This partially neutralized dispersion was spray dried in a FSD spray tower, the atomization taking place via a 1.2 mm two-material nozzle at an atomization pressure of 3.0 bar. The entry air temperature was 130° C. and the exit air temperature 59° C. The fines fraction was separated off during the spray drying and blown again in front of the spray nozzle, so that spray-dried particles with an average particle size of 200 μm resulted. During the spraying process, colloidal silicon dioxide with a BET surface area of 200 m$^2$/g was blown into the tower in an amount of 0.5%, based on the total mass of the polymer powder.

The spray-dried product was redispersed in water to give a spray suspension with a solids content of 20% by stirring using a paddle stirrer for 20 min. Measurement of the particle size by means of light scattering gave a value of 130 nm.

Example 5

1000 ml of an aqueous dispersion of polymer C with a solids content of 30% were mixed, with stirring, with 1.31 g of malonic acid. This corresponds to a degree of neutralization of 5 mol %. This partially neutralized dispersion was mixed with 200 ml of a 40% strength suspension of talc and spray dried in a FSD spray tower, the atomization taking place via a 1.2 mm two-material nozzle at an atomization pressure of 3.0 bar. The entry air temperature was 135° C. and the exit air temperature 61° C. The fines fraction was separated off during the spray drying and blown again in front of the spray nozzle, so that spray-dried particles with an average particle size of 210 μm resulted. The spray-dried product was redispersed in water to give a spray suspension with a solids content of 20% by stirring using a paddle stirrer for 15 min. Measurement of the particle size by means of light scattering gave a value of 141 nm for the polymer particles.

Example 6

1000 ml of an aqueous dispersion of polymer B with a solids content of 30% were admixed, with stirring, with 200 g of water, 100 g of talc, 20 g of red iron oxide and 10 g of polyvinyl alcohol and 36.5 ml of 1 molar hydrochloric acid. This preparation was homogenized using an Ultra-turrax for 20 min at 12 000 rpm and then spray dried in a FSD spray tower, the atomization taking place via a 1.2 mm two-material nozzle at an atomization pressure of 3.0 bar. The entry air temperature was 138° C. and the exit air temperature 62° C. The fines fraction was separated off during the spray drying and blown again in front of the spray nozzle, so that spray-dried particles with an average particle size of 220 μm resulted.

The spray-dried product was redispersed in water to give a spray suspension with a solids content of 20% by stirring using a paddle stirrer for 30 min. Measurement of the particle size by means of light scattering gave a value of 133 nm for the polymer particles.

Example 7

1000 ml of an aqueous dispersion of polymer B with a solids content of 30% were admixed, with stirring, with 15 g of polyvinyl alcohol, 6 g of docusate sodium and 3 g of colloidal silicon dioxide. This dispersion was spray dried in a FSD spray tower, the atomization taking place via a 1.2 mm two-material nozzle at an atomization pressure of 3.0 bar. The entry air temperature was 105° C. and the exit air temperature 48° C. The fines fraction was separated off during the spray drying and blown again in front of the spray nozzle. During the spraying process, colloidal silicon dioxide with a BET surface area of 200 m$^2$/g was blown into the tower in an amount of 1.0%, based on the total mass of the polymer powder. In a fluidized bed directly connected to the spray tower, the powder was after-dried at 45° C. The spray-dried particles had an average particle size of 210 μm.

The spray-dried product was redispersed in water to give a spray suspension with a solids content of 15% by stirring using a paddle stirrer for 20 min. Measurement of the particle size by means of light scattering gave a value of 170 nm.

Example 8

3.5 g of sodium dihydrogenphosphate were dissolved in 1000 ml of an aqueous dispersion of polymer A with a solids content of 30% and then spray dried in a spray tower. The atomization took place here via a 1.2 mm two-material nozzle at an atomization pressure of 3.0 bar. The drying gas was introduced tangentially in the entry region of the spray dryer and the dried product was separated off in a cyclone. The entry air temperature was 115° C. and the exit air temperature 55° C. The average particle size was 35 μm.

Redispersion of this preparation in water to give a 15% strength suspension using a propeller stirrer for 15 min gave rise to a particle size of the polymer particles of 138 nm.

Example 9

100 g of polymer powder prepared as in example 3 were mixed with 50 g of very finely ground talc, 4 g of indigotin lake and 2 g of succinic acid in a Turbula mixer.

Following the redispersion of this preparation in water to give a 15% strength suspension using a propeller stirrer, a particle size of the polymer particles of 150 nm was produced.

Example 10

The preparation produced as in example 9 was admixed with 15 g of triethyl citrate, stirred for two hours and applied to tablet cores by spraying.

Spraying Conditions:

| | |
|---|---|
| Machine | Horizontal drum coater |
| Entry air temperature | 54° C. |
| Spraying pressure | 0.2 MPa |
| Shaping air pressure | 0.1 MPa |
| Spray nozzle | Schlick 930/1 mm |
| Entry air rate | 200 m$^3$/h |
| Spraying rate | 30 g/min |

The invention claimed is:

1. A process for producing pulverulent coating compositions comprising:
  providing an aqueous polymer dispersion comprising
    i) as component A, a polymer obtained by radical polymerization of
      a) N,N-diethylaminoethyl methacrylate, and
      b) at least one radically polymerizable compound selected from esters of α,β-ethylenically unsaturated mono- and dicarboxylic acids with $C_1$-$C_8$-alkanols; and
  spray processing the aqueous polymer dispersion with a spraying apparatus in the presence of a drying gas to provide a powder, wherein an entry temperature of the drying gas into the spraying apparatus is at least 20° C. above a glass transition temperature and is at least 20° C. above a minimum film-forming temperature of the polymer and an exit temperature of the drying gas from the spraying apparatus is maintained at 40 to 85° C.

2. The process according to claim 1, wherein the entry temperature of the drying gas into the spraying apparatus is at least 40° C. above the glass transition temperature and is at least 40° C. above the minimum film-forming temperature of the polymer.

3. The process according to claim 1, wherein the entry temperature of the drying gas into the spraying apparatus is at least 20° C. above the dynamic glass transition temperature.

4. The process according to claim 3, wherein the entry temperature of the drying gas into the spraying apparatus is at least 40° C. above the dynamic glass transition temperature.

5. The process according to claim 1, wherein the entry temperature of the drying gas into the spraying apparatus is 100 to 140° C. and the exit temperature of the drying gas from the spraying apparatus is maintained at 45 to 70° C.

6. The process according to claim 1, wherein the exit temperature of the drying gas from the spraying apparatus is maintained within 5° C. of the minimum film-forming temperature.

7. The process according to claim 1, wherein the spray processing includes spray drying or agglomerating spray drying.

8. The process according to claim 1, wherein an acid or an acidic salt is added to the aqueous polymer dispersion before the spray processing or is added to the powder after the spray processing.

9. The process according to claim 1, wherein, after the spray processing, the resulting polymer powder is redispersed in water and admixed with an acid or an acidic salt.

10. The process according to claim 8, wherein the acid added is an acid or an acidic salt thereof which is decomposed or evaporated under the conditions of the spray processing.

11. The process according to claim 8, wherein, as a result of adding the acid or the acidic salt, the pH of the aqueous dispersion or of the powder is in the range from 5 to 9.

12. The process according to claim 11, wherein, by adding the acid or the acidic salt, the pH of the aqueous dispersion or of the powder is in the range from 6 to 8.

13. The process according to claim 1, wherein a further auxiliary is added to the aqueous polymer dispersion before the spray processing.

14. The process according to claim 1, wherein silicon dioxide is added to the resulting polymer powder during or after the spraying process.

15. A method of coating a pharmaceutical dosage form comprising applying a polymer powder obtained according to claim 1 as a coating composition to the pharmaceutical dosage form.

16. The method according to claim 15, wherein the coating composition is applied to the dosage form in the form of an aqueous dispersion obtained by redispersing the polymer powder.

17. The method according to claim 16, wherein redispersing the polymer powder comprises stirring the powder in water with a dispersing apparatus at revolutions of greater than 5000 rpm.

18. The method according to claim 16, wherein redispersing the polymer powder comprises stirring the powder in water with a dispersing apparatus at revolutions of less than 1000 rpm.

19. The method according to claim 15, wherein the coating composition further comprises one or more auxiliaries selected from the group consisting of aroma substances, taste-improving substances, sweetening agents, glidants, wetting agents, release agents, antisticking agents, stabilizers, antioxidants, pore formers, neutralizing agents, luster agents, dyes, pigments, disinfectants or preservatives, thickeners and plasticizers.

20. The method according to claim 16, wherein the polymer powder is ground on its own or together with additional auxiliaries before redispersing.

\* \* \* \* \*